(12) United States Patent
Izrailit

(10) Patent No.: US 10,582,647 B2
(45) Date of Patent: Mar. 3, 2020

(54) POWER SUPPLY UNIT

(71) Applicant: TETRA LAVAL HOLDINGS & FINANCE S.A., Pully (CH)

(72) Inventor: Iosif Izrailit, Newton, MA (US)

(73) Assignee: TETRA LAVAL HOLDINGS & FINANCE S.A., Pully (CH)

( * ) Notice: Subject to any disclaimer, the term of this patent is extended or adjusted under 35 U.S.C. 154(b) by 788 days.

(21) Appl. No.: 15/119,837

(22) PCT Filed: Jan. 21, 2015

(86) PCT No.: PCT/EP2015/051063
§ 371 (c)(1),
(2) Date: Aug. 18, 2016

(87) PCT Pub. No.: WO2015/124352
PCT Pub. Date: Aug. 27, 2015

(65) Prior Publication Data
US 2017/0064878 A1 Mar. 2, 2017

(30) Foreign Application Priority Data
Feb. 19, 2014 (SE) ...................................... 1450202

(51) Int. Cl.
*H05K 5/02* (2006.01)
*H05K 7/20* (2006.01)
(Continued)

(52) U.S. Cl.
CPC ............ *H05K 7/20909* (2013.01); *A61L 2/08* (2013.01); *A61L 2/087* (2013.01); *B65B 55/02* (2013.01);
(Continued)

(58) Field of Classification Search
CPC ........ H05K 7/20909; H05K 5/00; H05K 5/02; H05K 5/06; H05K 7/1457; H05K 7/202;
(Continued)

(56) References Cited

U.S. PATENT DOCUMENTS 3,699,394 A 10/1972 Schuler
5,057,648 A * 10/1991 Blough ................. H01L 25/165
174/561

(Continued)

FOREIGN PATENT DOCUMENTS

JP S51-035899 A 3/1976
JP S63-310306 A 12/1988
(Continued)

OTHER PUBLICATIONS

Office Action (Notification of Reasons for Refusal) dated Jan. 15, 2019, by the Japanese Patent Office in corresponding Japanese Patent Application No. 2016-552964 and an English Translation of the Office Action. (11 pages).

(Continued)

*Primary Examiner* — Angel R Estrada
(74) *Attorney, Agent, or Firm* — Buchanan Ingersoll & Rooney PC

(57) ABSTRACT

Power supply unit, in particular for a sterilization device, comprising a housing and an electric system, wherein the electric system is located within the housing, wherein the housing is filled with an insulation gas, in particular nitrogen, wherein the insulation gas is adapted to electrically insulate the electric system.

15 Claims, 13 Drawing Sheets

Figure 1A:
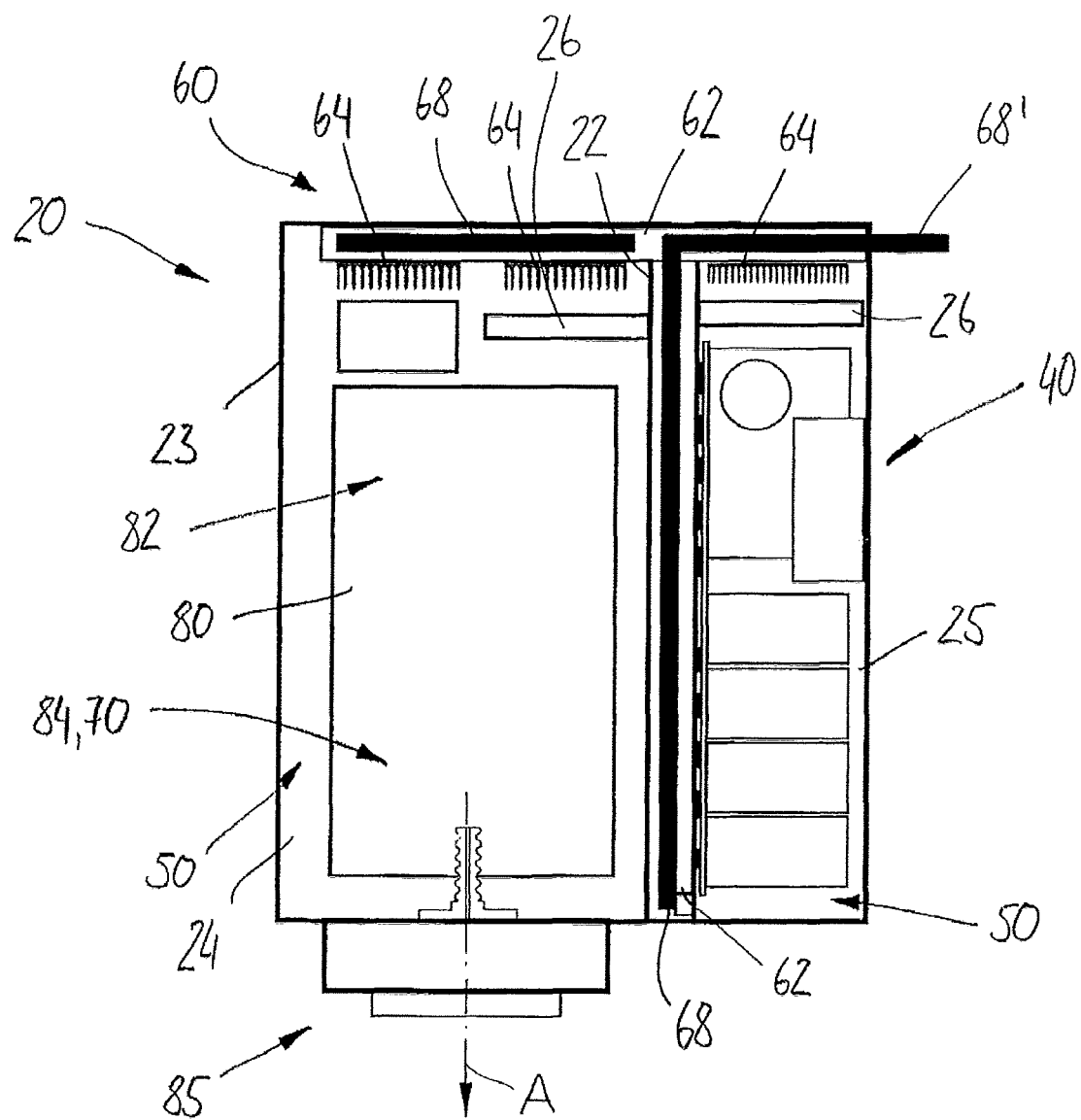

(51) Int. Cl.
*A61L 2/08* (2006.01)
*H05K 7/14* (2006.01)
*B65B 55/02* (2006.01)
*H05K 5/06* (2006.01)

(52) U.S. Cl.
CPC ............. *H05K 5/06* (2013.01); *H05K 7/1457* (2013.01); *H05K 7/202* (2013.01); *H05K 7/209* (2013.01)

(58) Field of Classification Search
CPC ........... H05K 7/209; A61L 2/08; A61L 2/087; B65B 55/02; H02G 3/08; H02G 3/081
USPC .......... 174/50, 50.5, 50.51, 50.52, 520, 521, 174/535, 548, 559, 560, 137 R, 138 R, 174/176, 17 GF, 17 R, 15.1
See application file for complete search history.

(56) References Cited

U.S. PATENT DOCUMENTS

| | | | | |
|---|---|---|---|---|
| 5,136,856 | A * | 8/1992 | Yamamoto | G06F 1/206 174/15.1 |
| 5,792,984 | A * | 8/1998 | Bloom | H01L 23/10 174/564 |
| 6,438,250 | B1 * | 8/2002 | Johannet | H05K 9/00 174/17 LF |
| 2010/0202111 | A1 | 8/2010 | Liang | |
| 2014/0247538 | A1 | 9/2014 | Uchii et al. | |
| 2014/0346145 | A1 | 11/2014 | Piccoz et al. | |
| 2017/0056539 | A1 | 3/2017 | Mellbin | |
| 2017/0064853 | A1 | 3/2017 | Izrailit | |
| 2017/0065734 | A1 | 3/2017 | Izrailit | |
| 2017/0065735 | A1 | 3/2017 | Mellbin | |

FOREIGN PATENT DOCUMENTS

| | | |
|---|---|---|
| JP | H09-084260 A | 3/1997 |
| JP | 2009-528228 A | 8/2009 |
| JP | 2013-171947 A | 9/2013 |
| WO | 2007/099120 A1 | 9/2007 |
| WO | WO 2012/080269 A1 | 6/2012 |
| WO | WO 2012/160155 A1 | 11/2012 |
| WO | WO 2013/004564 A1 | 1/2013 |
| WO | WO 2013/076892 A1 | 5/2013 |
| WO | WO 2013/136015 A1 | 9/2013 |

OTHER PUBLICATIONS

International Search Report (PCT/ISA/210) dated Apr. 29, 2015, by the European Patent Office as the International Searching Authority for International Application No. PCT/EP2015/051063.
Written Opinion (PCT/ISA/237) dated Apr. 29, 2015, by the European Patent Office as the International Searching Authority for International Application No. PCT/EP2015/051063.
Office Action dated Sep. 18, 2014 by the Swedish Patent Office in Swedish Priority Application No. 1450202-5.
An application entitled "Power Supply Unit", naming Iosif Izrailit as inventor.
An application entitled "Power Supply", naming Håkan Mellbin as inventor.
U.S. Appl. No. 15/119,837 (U.S. Application Publication No. 2017/0064853), filed Aug. 18, 2016, entitled "Power Supply Unit" and naming Iosif Izrailit as the inventor.
U.S. Appl. No. 15/119,966 (U.S. Application Publication No. 2017/0065734), filed Aug. 18, 2016, entitled "Power Supply Unit" and naming Iosif Izrailit as the inventor.
U.S. Appl. No. 15/119,996 (U.S. Application Publication No. 2017/0065735, filed Aug. 18, 2016, entitled "Power Supply" and naming Håkan Mellbin as the inventor.
U.S. Appl. No. 15/120,079 (U.S. Application Publication No. 2017-0056539), filed Aug. 18, 2016, entitled "Sterilization Device and an Electron Beam Emitter" and naming Håkan Mellbin as the inventor.

* cited by examiner

POWER SUPPLY UNIT

This invention relates to a power supply unit, in particular for a sterilization device, to a sterilization device, in particular for packaging material, and to a method to electrically insulate a power supply unit, in particular for a sterilization device.

Electron beam irradiation has been considered as a promising alternative for sterilizing purposes for which wet chemistry involving hydrogen peroxide has been the traditional technical platform. Electron beam irradiation provides sufficient sterilization of e.g. packaging material eliminating the negative consequences of wet chemistry within e.g. a packaging machine. However, sterilization devices or electron beam emitters, respectively, known from the prior art, are in general heavy, quite big and uncomfortable to use. In particular, they are often not adapted to comply with the requirements of the packaging industry.

For example oil used as insulation medium for insulating the power supply unit against the housing can cause problems with regard to food industry applications or in the medical/biological area as the oil could leak out and damage or pollute the material that has to be sterilized. In addition, the usage of oil increases the weight of the components. However, the electron beam emitters and the corresponding components, as for example the power supply unit, should be preferably light as they are often arranged on movable parts, e.g. on a movable carousel.

The power supply unit generates the high voltage that is necessary to operate the electron beam emitter. However, generating this high voltage produces heat. Therefore, also solutions have to be found to cool the whole electric system and to provide reliable operation conditions inside the power supply unit or in the sterilization device, respectively.

The present invention provides a power supply unit, in particular for a sterilization device, a sterilization device, in particular for packaging material with an improved insulation and cooling conditions inside the power supply unit. Further, a method to electrically insulate a power supply unit is provided, in particular for a sterilization device, to maintain good insulation and cooling conditions inside the power supply unit as well as a power supply unit or a sterilization device, respectively, that provides high flexibility, easiness in handling and cost effectiveness.

It is achieved by a power supply unit according to claim 1, by a sterilization device according to claim 13 and a method to electrically insulate a power supply unit according to claim 14. Additional advantages and features of preferred embodiments of the current invention are defined in the dependent claims.

According to the invention, a power supply unit, in particular for a sterilization device, comprises a housing and an electric system, wherein the electric system is located within the housing, characterized in that the housing is filled with an insulation gas, wherein the gas is adapted to electrically insulate the electric system from the housing or components of the electric system thereof from each other. The use of insulation gas improves the dielectric strength of the electric system and the housing or of parts of the electric system. The power supply unit is connected or connectable, respectively, to an electron beam emitter.

The term insulation refers to a conductive separation between two elements. An insulator or isolator is, when used within its specification a substantially non-conductive element or material, being able to electrically separate to conductive elements from each other.

The combination or unity of the power supply unit and the electron beam emitter is defined herein as sterilization device. There are no limitations concerning the number of electron beam emitters that is connected or connectable to one power supply unit. However, without limiting the generality, the following features refer for the sake of convenience to a sterilization device that comprises one power supply unit and one electron beam emitter.

According to one or more embodiments the electron beam emitter comprises an electron generator for emitting charge carriers, such as electrons. The electron generator is generally enclosed in a hermetically sealed vacuum chamber. The vacuum chamber is provided with an electron exit window. Furthermore, the electron generator comprises a cathode housing and a filament. In use, an electron beam is generated by heating the filament. When an electrical current is fed through the filament, the electrical resistance of the filament causes the filament to be heated to a temperature in the order of 2,000° C. This heating causes the filament to emit a cloud of electrons. The electrons are accelerated towards the electron exit window by means of a high potential difference between the cathode housing and the exit window. Subsequently, the electrons pass through the electron exit window and continue towards the target area, e.g. a part of a packaging material that has to be sterilized.

The high potential difference is for example created by connecting the cathode housing and the filament to the power supply unit providing a high potential and by connecting the vacuum chamber to ground potential. Of course other potentials can be used as well, the difference between the potentials give the voltage accelerating the electrons emitted by the filament. Unless otherwise stated the term voltage shall mean the difference between a potential provided by a source and the ground potential.

The voltage which the power supply unit provides usually lies in the range of about 80 to 115 kV. However, also voltages in the range of about 75 to 150 kV are generated, according to one or more embodiments of the invention. An electron beam emitter like this can be used for sterilization of packaging material, food, biological or medical devices etc.

There are no limitations concerning the content of the packaging material. The content can be liquid or solid. There are also no imitations concerning the use of the sterilization device or the electron beam emitter itself, respectively. Thus, the electron beam emitter or the sterilization device, respectively, can be used for inside and/or outside sterilization.

According to one embodiment, the sterilization device or the power supply unit, respectively, is used for inside and/or outside sterilization of packaging containers, e.g. made of carton and/or plastics. An electric connection between the power supply unit and the electron beam emitter is provided in one embodiment by a high voltage output connector of the power supply unit. Such connector provides certain insulation and comprises material as well as a design able to withstand very high voltages. In another embodiment the power supply unit and the electron beam emitter are connected and the power supply unit is hermetically sealed and flushed with the insulation gas. A sufficient space, e.g. around 30 mm between any wires operating at high voltages and the housing is selected and a barrier between the emitter and the all connection wires established. In such environment the connection between the power supply unit and the emitter can be made with a normal connector without considering special requirements for high voltage operation.

Advantageously, the high voltage output connector is adapted to provide a hermetic connection. The connection may be a form and/or force fit connection e.g. using screws and/or bolts (in combination with appropriate openings). The high voltage output connector provides a connection to the electric system or to at least one part of the electric system, respectively, inside the housing of the power supply unit. Generally speaking, the electric system is adapted to generate the high voltage that is needed for the sterilization process.

However, if high potentials or voltages are generated, electric insulation is an issue. In particular, corona has to be avoided. Corona discharge is an electrical discharge brought on by the ionization of a medium, such as a gas, surrounding a conductor that is electrically energized. Corona discharge is a process by which electrons flow from an electrode with a high potential into an easy ionizable neutral fluid so as to create a region of plasma around the electrode. The ions generated eventually pass charge to nearby areas of lower potential. The discharge will occur when the strength (potential gradient of the electric field) around the conductor is high enough to form a conductive region, but not high enough to cause electrical break down or arcing to nearby objects. However, in the present context also electric arcs or arc discharges have to be avoided as they can damage the sterilization device and its components. Additionally, in particular personnel working with the sterilization device have to be protected.

The present invention proposes among other aspects to use insulation gas in the housing to improve the dielectric strength of the power supply unit or parts thereof. In one embodiment, nitrogen is used as an insulation gas. Nitrogen is a dielectric gas that is adapted to prevent or rapidly quench electric discharges. Nitrogen has a shorter mean free path between its electrons than air. The mean free path is the average distance travelled by a moving particle between successive impacts, which modify its direction or energy or other particle properties. In another embodiment carbon dioxide is used as insulation gas. Both gases are chemically relatively inactive and does not cause corrosion of electronic components. Thus, the insulation properties are much better than the ones of e.g. air with oxygen included.

A big advantage of the usage of the insulation gas, such as nitrogen, contrary to the usage of e.g. an insulation oil is that the gas cannot leak out and drop on the material that has to be sterilized. The material that has to be sterilized cannot be damaged or polluted by the insulation medium/gas. This is a very big advantage in particular with regard to the food packaging industry.

Another big advantage is the lower density of the insulation gas contrary to the density of a liquid insulation material, such as oil. Using insulation gas, pressurized or unpressurized, enables a weight reduction in the range of about 20%. As already mentioned, the sterilization devices are in general arranged on moving parts such as carousels or the like. These carousels move very fast and have for example to be lifted, accelerated, stopped etc. Thus, the weight of the sterilization device should be reduced as much as possible. This weight reduction can advantageously be realized by the usage of insulation gas, such as nitrogen or carbon dioxide.

However, the above mentioned mean free path between the electrons of the insulation gas, such as nitrogen, is still bigger than that one of for example oil. Depending on the specific circumstances and the structure and design of a high voltage power supply unit, it might be suitable to implement further elements to improve the dielectric strength of the power supply unit.

In the following, additional aspects are listed that can be realized according to one or more embodiments:

a) The electric system or parts of the electric system, respectively, is generally installed on specific boards that are arranged inside the housing. According to one or more embodiments the material that is used for these boards may comprise FR4. According to an embodiment a maximum acceptable electric field parallel to a lamination of the board material is approximately 2 kV/mm.

b) The maximum acceptable electrical field for the components that are arranged on the board is approximately 6-8 kV/mm (of conductor radius).

c) The above mentioned values can be increased by factor of 3 to 4 by coating the conductive surface of the electric components having high dielectric strength, e.g. polymer compounds. For board insulation a dielectric polymer compound can be used. Examples may comprise epoxy resins, polyester resins, silicones, polypropylenes and liquid organosilicon rubbers, which can also withstand the higher temperatures of such power supply in operation. Especially for corona prevention a polymer compound with a small amount of conductive additive should be used. Additives may include heat stabilizing additives or conductive additives such a Bariumtitanate, Carbon, nanocomposites with microfillers and the like.

According to one aspect of the invention, the insulation gas is pressurized. For instance, the insulation gas can have a higher partial pressure than the surrounding pressure. This improves the insulation properties of the dielectric gas. The pressure may lay within a range of about 1.5 to 5 bar (meant is always absolute pressure). In an embodiment the pressure is about 3.5 to 4.0 bar, so at least 2.5 bar above the normal pressure outside the housing. Pressurized nitrogen provides a good and reliable insulation. At 2.5 bar a breakdown voltage is over 8 kV/mm for a 3 mm radius test electron.

According to another aspect, the insulation gas, in particular the nitrogen, and especially in particular the pressurized nitrogen is also dehumidified. Low humidity inside the housing increases breakdown voltage even more and decrease surface leakage and corona. Decreasing the oxygen content also significantly reduces a risk of generation of ozone and increases the life expectancy of the electric system. Nitrogen with 0.1-1% contamination is suitable for this application according to one or more embodiments. Compared to the usage of (insulation) oil a weight reduction in the range of about 20% can be achieved.

Expediently, the power supply unit comprises a heat absorber unit, wherein the heat absorber unit is formed by at least one plate. The plate can be made of metal, for example aluminium or copper. In general, a material should be preferred that provides a good conduction of heat. According to one aspect of the invention parts of the electric system are directly mounted on the at least one plate or are at least in (heat conductive) contact with the at least one plate. Thus, the heat that is generated by parts of the electric system can be absorbed and transferred by the heat absorber unit or by the at least one plate.

However, the heat absorber unit is also adapted to absorb heat from inside the housing, in particular from the insulation gas. Therefore, expediently the heat absorber comprises at least one heat exchange element, wherein the heat exchange element is advantageously arranged at the at least one plate. The at least one heat exchange element is preferably a component with a large surface. The surface is, in other words, a large heat conducting surface. As a consequence, the at least one heat exchange element can absorb heat from the inside of the housing, in particular from the insulation gas, wherein the at least one heat exchange element transfers the absorbed heat to the heat absorber unit, as the heat exchange element is preferably in contact with the heat absorber unit or the at least one plate, respectively.

According to one or more embodiments at least parts of the electric system are arranged on a board wherein the board is arranged at the at least one plate. The board can be for example made of FR4. According to one aspect of the invention the board is a power converter board and adapted to provide a high potential or output to a high voltage connector. Parts of the electric system can be arranged at the power converter board. The power converter board can also comprise conductors etc. In general, the (power converter) board produces also heat. However, as it is preferably in contact with the at least one plate the heat of the (power converter) board can be transferred to the plate. The plate and the (power converter) board do not have to have direct contact. It may be sufficient that they are at least arranged close side by side, e.g. by a form and/or force fit connection. However, direct contact is also possible and enhances heat transfer.

According to one or more embodiments the housing comprises an inner wall, wherein the inner wall separates the housing in a first chamber and at least one second chamber, wherein the at least one plate is advantageously arranged at the inner wall. Some parts of the electric system are arranged in the first chamber and other parts of the electric system are arranged in the second chamber. According to one aspect of the invention both chambers are filled with the insulation gas. The two chambers can be connected to each other. So insulation gas can stream for example from the first chamber to the second chamber and vice versa. In antother embodiment the two chambers are separated. This can be an advantage if different insulation conditions shall be realized in the two chambers. For example, different pressures of the insulation gas or different humidity levels can be provided in each chamber.

In addition, one chamber can be adapted to process, handle or generate high potentials or voltages, wherein the other chamber can be adapted to handle lower voltages. In general, the housing itself is formed by outer walls, wherein the material of the walls (inner and/or outer walls) can comprise a metal, e.g. aluminium, steel, but also plastic, fibre reinforced material etc or combinations thereof. According to one or more embodiments the housing is made of welded stainless steel, wherein a top end of the housing is expediently movable attached and sealed with appropriate o-rings. Alternatively or in addition a liquid gasket can be used. Advantageously, the insulation gas, such as nitrogen, cannot leak, even if it is pressurized. A detachable top end or in general a detachable part of the housing enables easy maintenance. According to on or more embodiments the power supply unit can comprise a diagnostic system that is adapted to indicate e.g. an insulation gas leakage or other problems that could occur during operation of the power supply unit.

According to another aspect of the invention, the insulation gas is a dielectric gas with a high dielectric strength such as nitrogen, carbon dioxide, $SF_6$ or other halogens.

Expediently, the heat absorber unit comprises at least one cooling channel, wherein the cooling channel is adapted to cool the at least one heat exchange element, the board, and/or the at least one plate. According to one aspect of the invention, the at least one cooling channel is integrated in the at least one plate. In other words, the plates may have one or more cooling channels. To improve the heat transfer expediently a cooling medium, such as gas or water, flows through the cooling channel(s). Therefore, the cooling channel has an inlet and an outlet. However, the cooling channel does not have to be integrated in another component as for example the plate. It can be a separated component that is located within the housing.

According to another aspect of the invention the housing comprises means for conveying the insulation gas, in particular a fan, wherein the conveyed insulation gas provides a cooling effect. One advantage of that is that a flow of insulation gas can be created. The insulation gas and in particular the flow of insulation gas provides expediently cooling properties. In other words, the insulation gas can absorb heat from the electric system or from parts of the electric system, respectively. Thus, preferably a cooling effect is provided by the insulation gas. It goes without saying that the insulation gas that for example surrounds a part of the electric system, does heat up itself. Therefore, it is a big advantage that the housing comprises means for conveying the gas. Thus, it can be made sure that the insulation gas that has heated up is for example blown away from the hot part of the electric system by the fan. Vice versa, it can be made sure by using the means for conveying the gas, in particular the fan, that always insulation gas that has not yet been heated up surrounds a part of the electric system that produces heat. Doing this it can be ensured that the insulation gas that surrounds the part of the electric system that produces heat can still absorb heat.

According to another aspect of the invention the housing comprises at least one heat source, wherein the means for conveying the insulation gas are adapted to establish an insulation gas flow that is directed at least from the at least one heat source to the at least one heat exchange element. Heat sources are these parts of the electric system that produce heat, as already described before. It is an advantage of the above described insulation gas flow that it can transfer its absorbed heat to the at least one heat exchange element. By transmitting the heat to the at least one heat exchanged element the insulation gas flow is cooled itself. According to one or more embodiments a temperature drop of the cooled insulations gas (at the heat exchange element) lies within a range of about 20 to 25° C. As a consequence the power supply unit can reliably be operated in ambient conditions up to 60° C. and more. It goes without saying that the means for conveying the insulation gas, in particular the fan is also adapted to bring the cooled insulation gas from the at least one heat exchange element (back) to the at least one heat source.

According to another aspect of the invention, the cooled insulation gas flow is at first guided to these parts of the electric system that produce the most heat. In other words, the insulation gas flow is at first guided to the "biggest" heat sources. In general, such heat sources may comprise the high voltage parts of the electric system. In an embodiment the housing contains guidance element for guiding the gas flow to such sources. The guidance elements may comprise baffles, guiding plate or deflectors and the like. The guidig elements should be in thermal contact with the housing as to allow heat transfer.

According to the invention it has to be made sure that during this "guidance" the cooled insulation gas flow heats up as little as possible. In one embodiment, the insulation gas flow is guided along the outer wall (inside the housing) for example. It goes without saying that a plurality of means for conveying the gas, in particular fans, can be provided. As a consequence, also a plurality of insulation gas flows can be established inside the housing. The above mentioned features and advantages apply to the housing in general and also—if provided—to different chambers of the housing.

Expediently, the insulation gas flow is a circulating insulation gas flow. Related to the housing or one of the chambers the circulating insulation gas flow can be established as follows. According to one or more embodiments the housing as well as the first and the second chamber (if provided) extend along a longitudinal axis. Thus, the housing has a top end and a bottom end, wherein the bottom end may comprise the above mentioned high voltage output connector. The circulating insulation gas flow can be established by providing for example a fan near the top end of the housing. According to one aspect of the invention, the fan is located basically in the middle of the housing, wherein the gas flow that is established by the fan moves from the bottom end to the top end. The at least one heat exchange element is located over the fan. As a consequence, the gas flow hits the at least one heat exchanged element and separates at the at least one heat exchange element in a plurality (at least, for example, two) of outer insulation gas flows that move from the top end to the bottom end of the housing, preferably along the outer walls of the housing. However, a circulation insulation gas flow as described before can also be established, if the insulation gas flow that is created by the fan does not move along the longitudinal axis.

According to another aspect of the invention the electric system comprises a voltage multiplier. In particular, at least one voltage multiplier, especially two or more voltage multiplier are provided. These may comprise discrete or integrated circuitry or a combination thereof. In general, the electric system comprises power electronic components, high voltage components and control system components. According to one or more embodiments the power electronic components are directly arranged at the at least one plate. For cooling of the high voltage components, wherein the voltage multiplier is an example of one part of the high voltage components, the insulation gas flow is used. To provide appropriate cooling conditions for the high voltage components, the at least one heat exchange element has a performance of about 200 W (water to nitrogen) heat transfer. For cooling of the control system components also an insulation gas flow in combination with a heat exchange element is expediently used. The heat exchange element may have a performance of about 60 W (water to nitrogen). Both heat exchange elements are preferably in contact with a water cooled plate or with water cooled plates, respectively. Preferably, the high voltage components are arranged within the first chamber, wherein the control system components and the power electronic components are arranged in the second chamber. Thus, each of the chambers has preferably its own heat exchange element and its own fan.

The voltage multiplier comprises at least a lower voltage area and a higher voltage area. In general, the voltage multiplier is an electrical circuit that converts A/C (alternating current) electrical power from a lower voltage to a higher D/C voltage. As already mentioned, the voltage multiplier or the voltage multipliers, respectively, generate voltages in the range of about 75 to 150 kV. Thus, the lower voltage area lies within a range up to 70 to 90 kV, wherein the voltage of the higher voltage area lies within a range of about 80 to 150 kV. According to one aspect of the invention, the lower voltage area is oriented or directed, respectively, towards the at least one heat exchange element. In combination with the above described insulation gas flow it can be ensured that the insulation gas flow is directed from the at least one heat source to the at least one heat exchange element.

In this context, the higher voltage area is the heat source. This part is advantageously directed to the bottom of the housing or the first chamber, respectively. The insulation gas flow should be as cold as possible during its first contact with the higher voltage are (of the voltage multiplier). Concerning the longitudinal axis of the housing or the first chamber, respectively, the lower voltage area could be directed or oriented towards the top end of the housing, wherein the higher voltage area could be directed or oriented towards the bottom end of the housing. As a consequence, the voltage multiplier or the voltage multipliers, respectively, can be ideally cooled by the (circulating) insulation gas flow, as described before.

According to the invention a sterilization device, in particular for a packaging material, comprises a power supply unit and an electron beam emitter, wherein the power supply unit comprises a housing and an electric system, wherein the electric system is located within the housing and wherein the electric system is adapted to electrically supply the electron beam emitter, characterized in that the housing is filled with an insulation gas, in particular nitrogen, wherein the insulation gas is adapted to electrically insulate the electric system.

According to the invention a method to electrically insulate a power supply unit or parts thereof, in particular for a sterilization device, with an insulation gas, in particular nitrogen, comprises a housing and an electric system, wherein the insulation gas is adapted to electrically insulate the electric system, and wherein the electric system is located within the housing, comprising the steps:

reducing air pressure inside the housing;
filling the housing with the insulation gas, in particular nitrogen.

According to one or more embodiments the air pressure inside the housing or chamber, respectively, should be minimized from starting pressure (in general about 1 bar) to about 0.002 or 0.001 bar, e.g. using an appropriate vacuum pump. According to one or more embodiments the vacuum pump is connected to an appropriate port of the housing, in particular a charging port. After this step, the housing or chamber, respectively, can be filled with the insulation gas, such as nitrogen, up to a pressure of about 2.5 or 3 bar above normal atmospheric pressure. At least, the vacuum pump can be disconnected, wherein the charging port should be hermetically sealed.

The power supply unit according to the invention can include the features and advantages of the sterilization device according to the invention and of the method to electrically insulate a power supply unit according to the invention and vice versa.

Additional aspects and features of the current invention are shown in the following description of preferred embodiments of the current invention with reference to the attached drawings. Single features or characteristics of respective embodiments are explicitly allowed to be combined within the scope of the current invention.

Figure 1B:
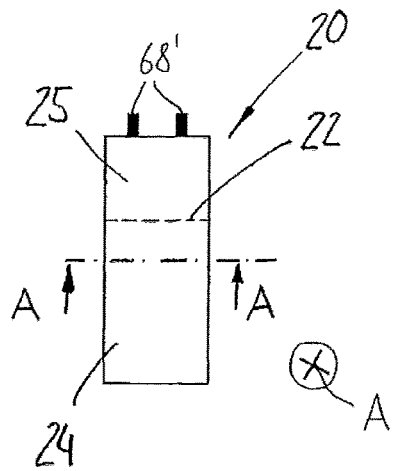
Figure 1C:
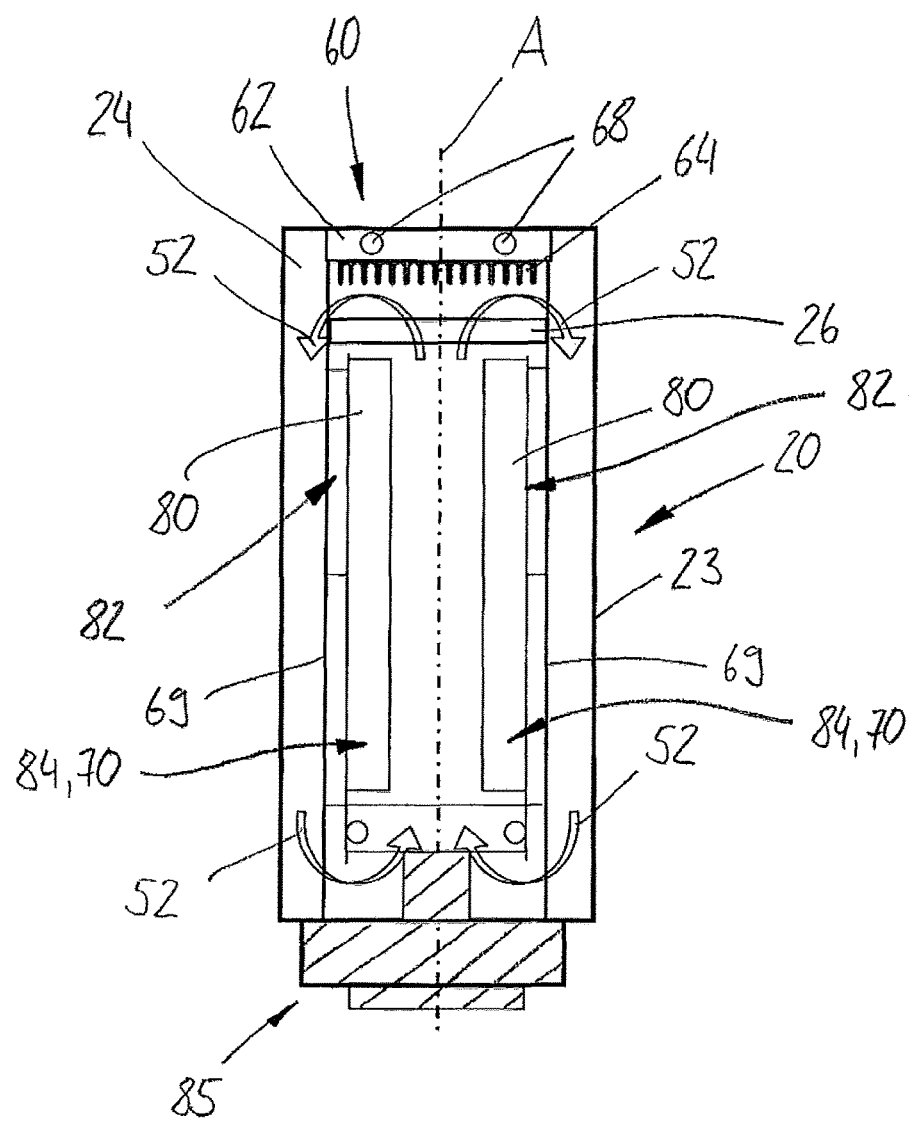
Figure 2A:
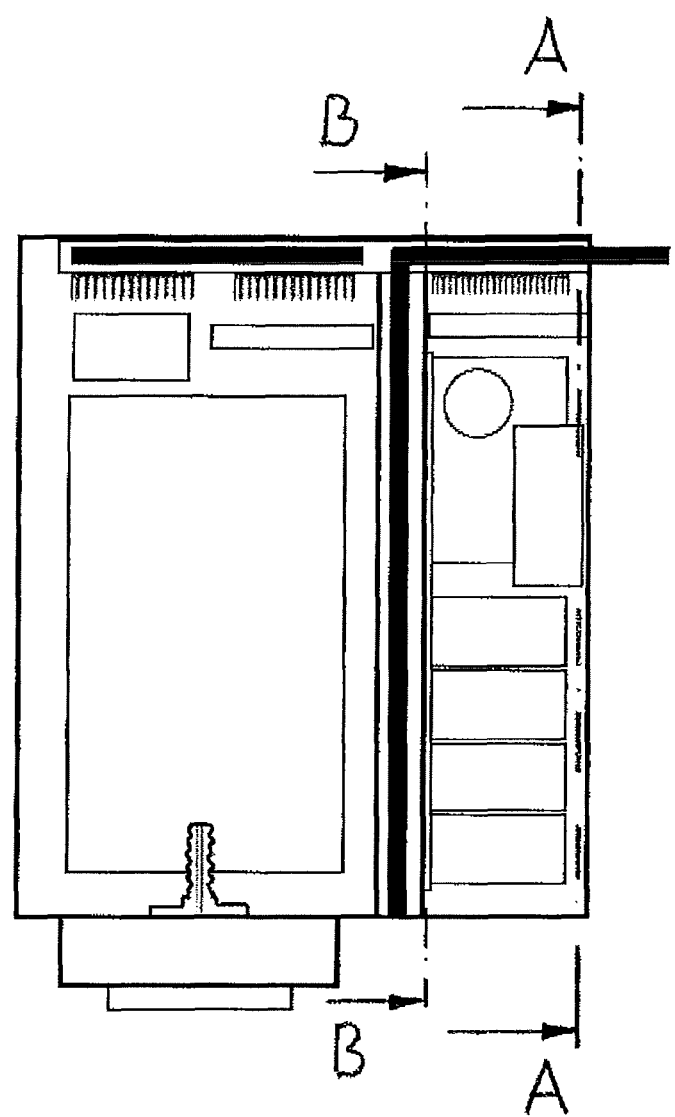
Figure 2B:
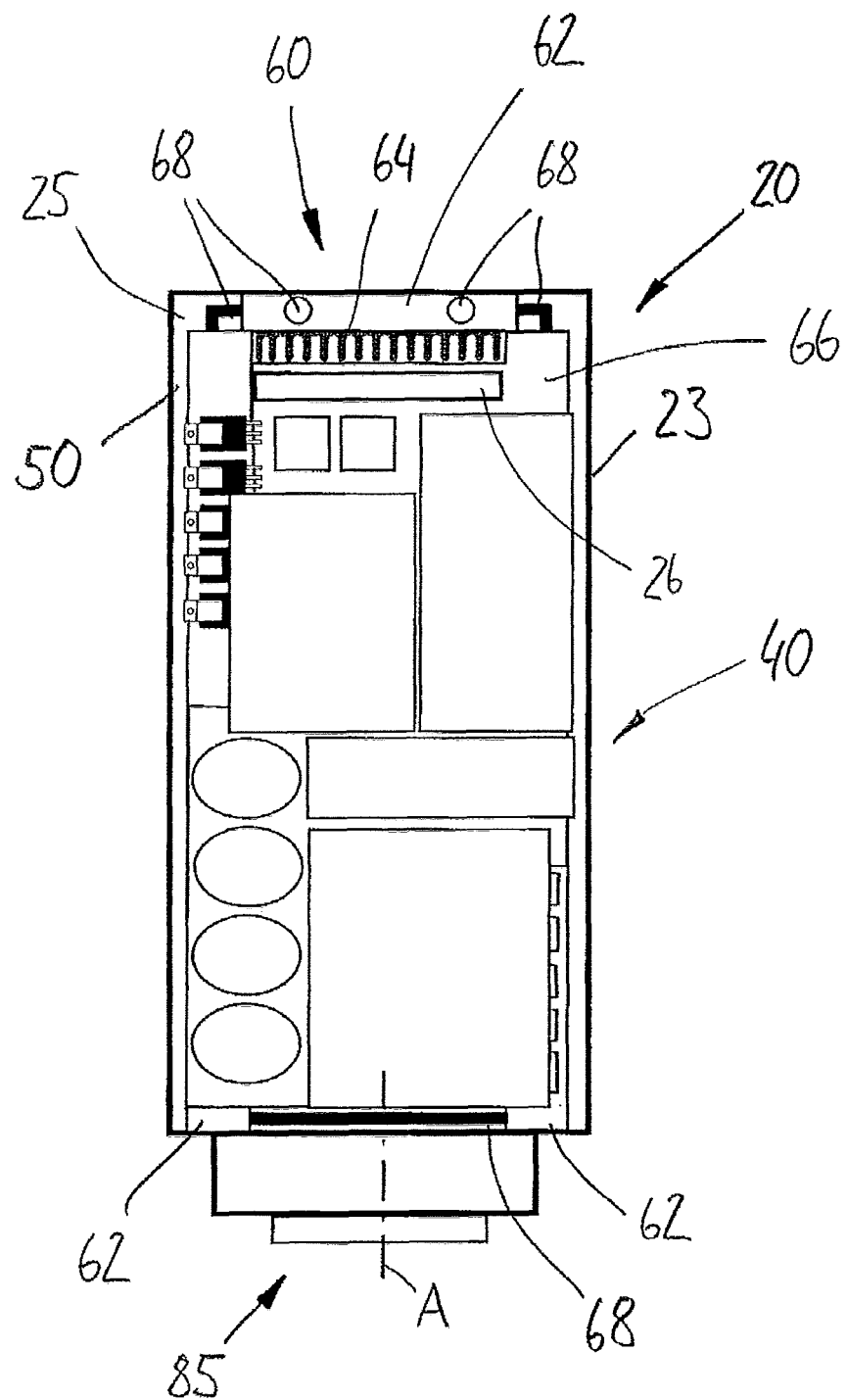
Figure 2C:
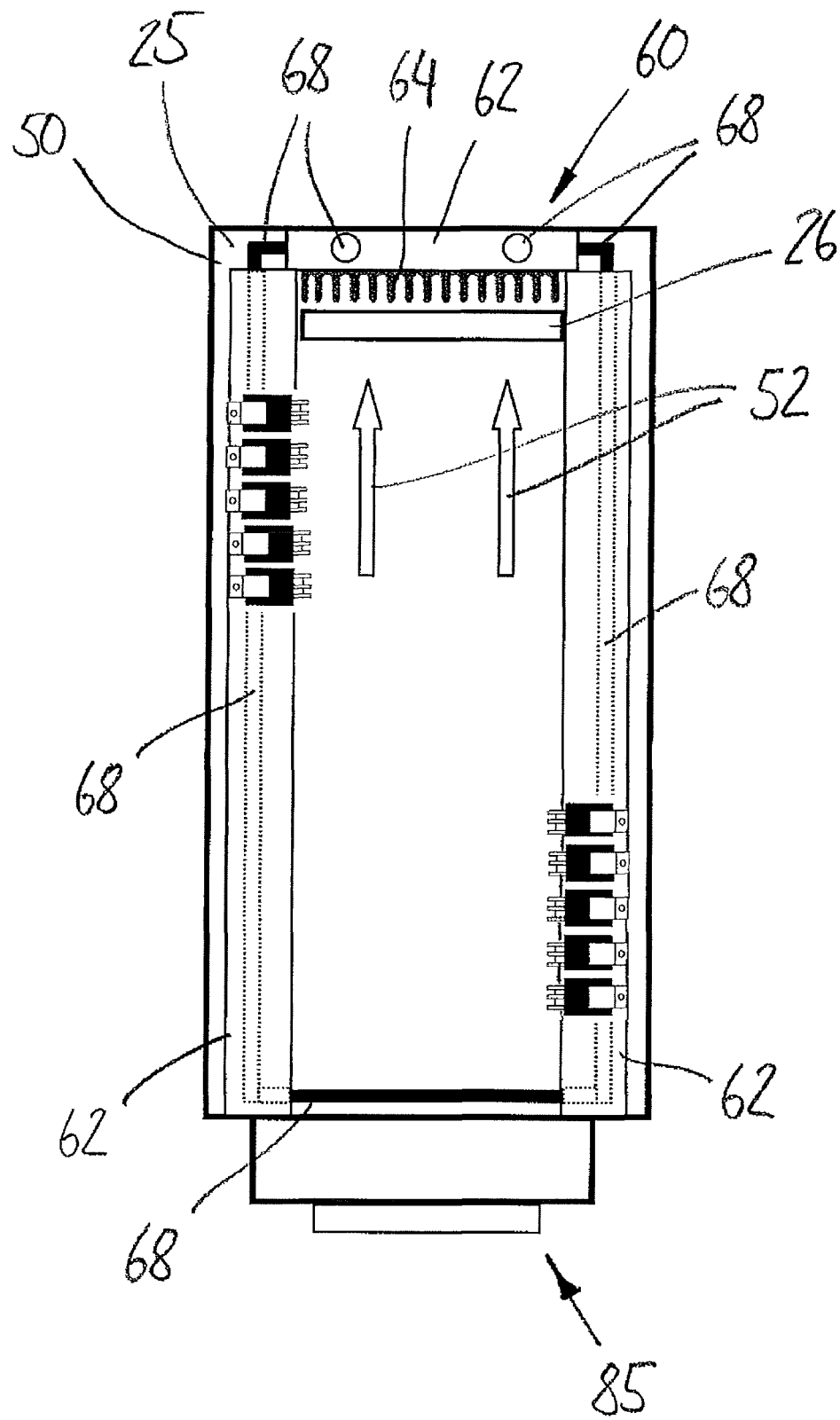
Figure 3A:
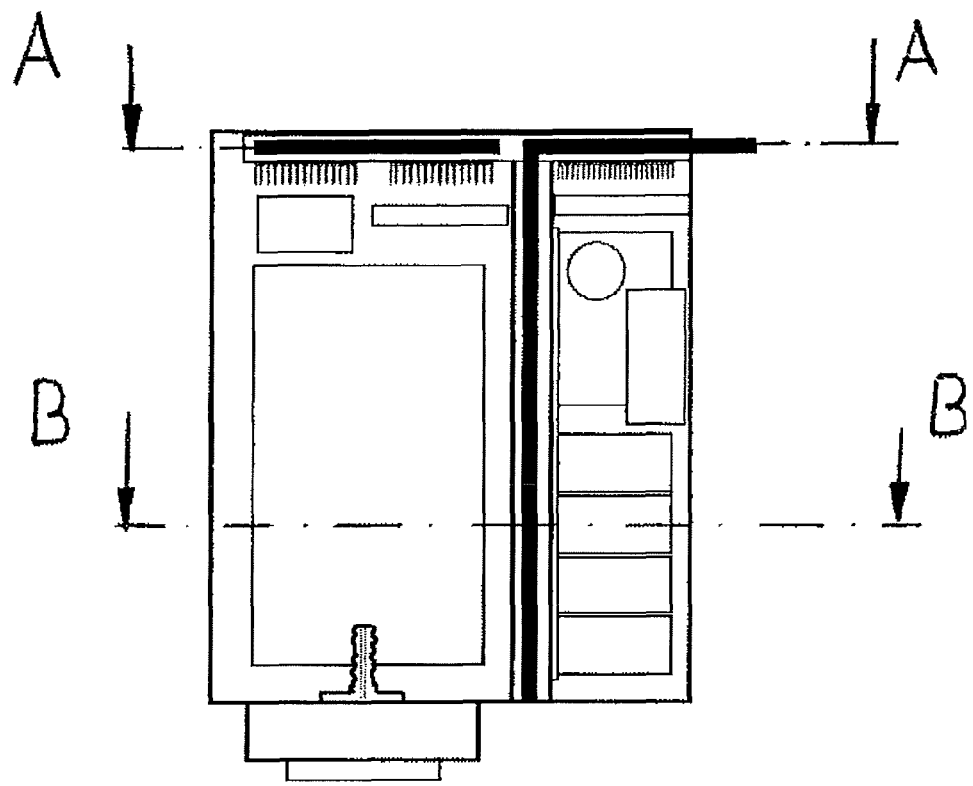
Figure 3B:
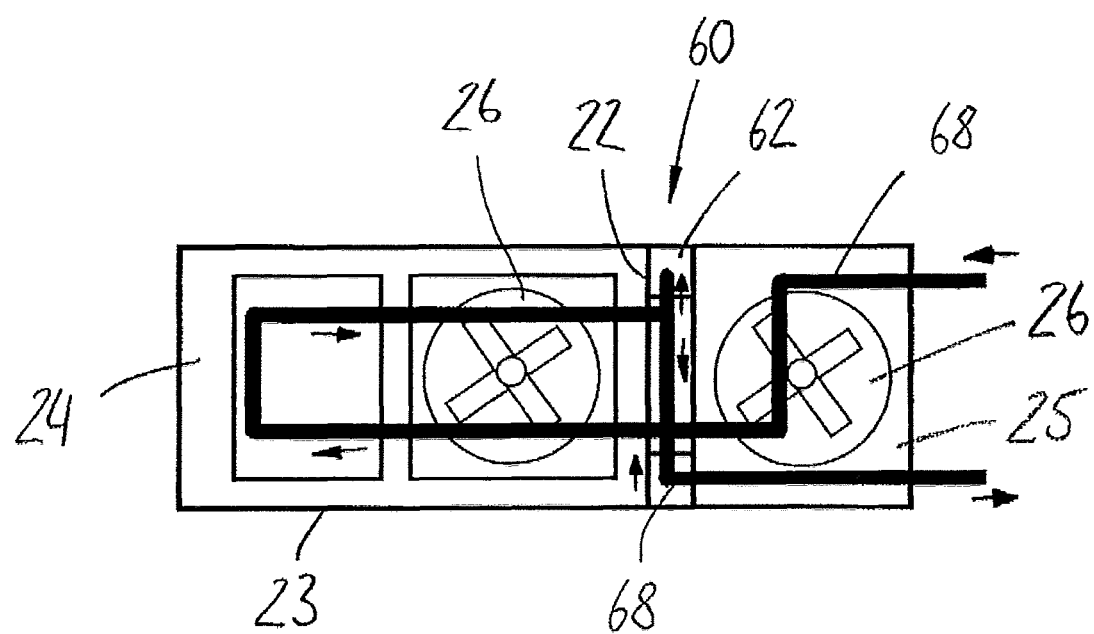
Figure 3C:
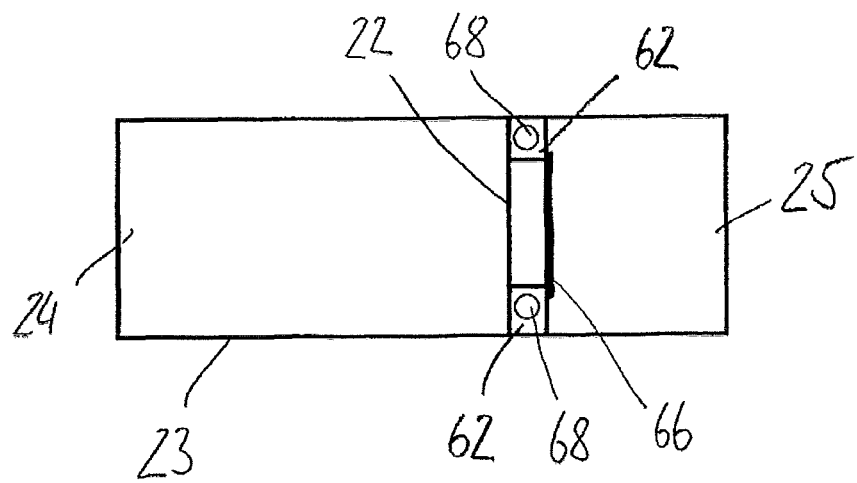
Figure 4:
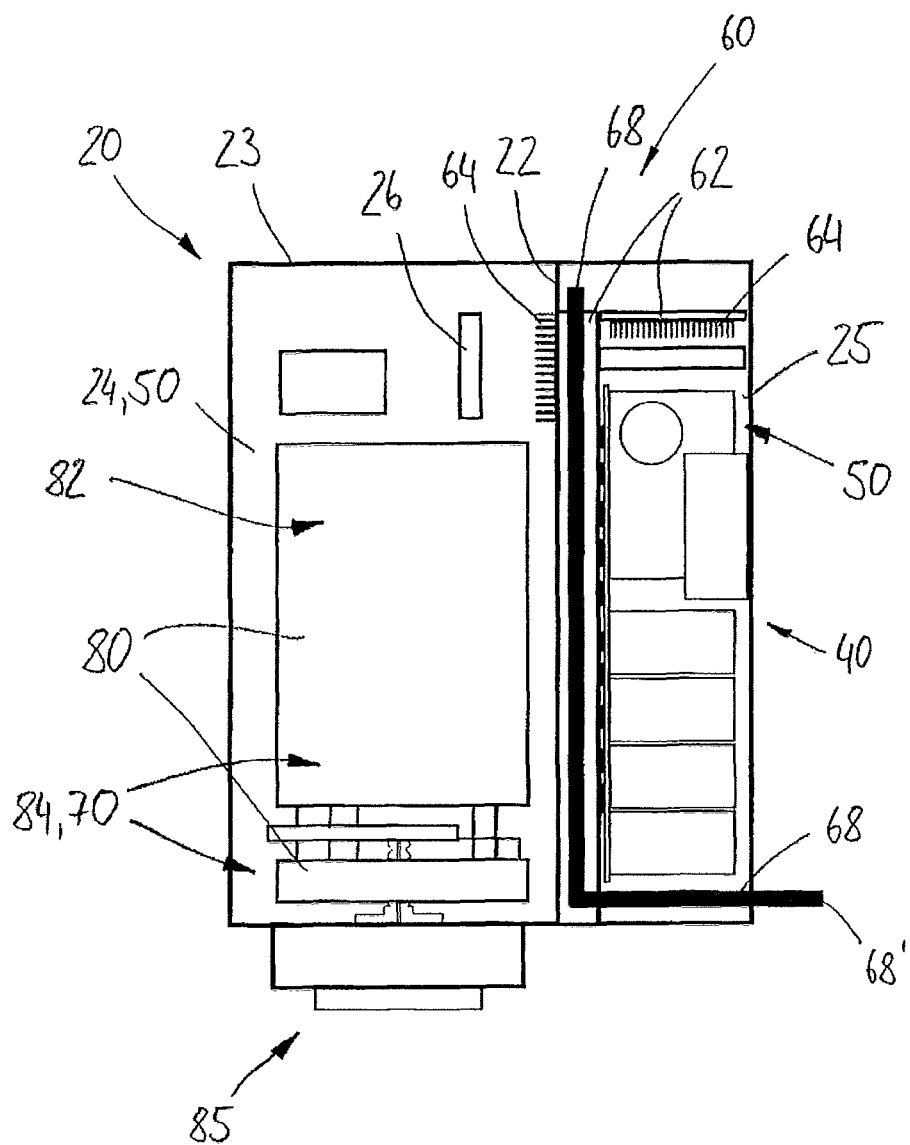
Figure 5:
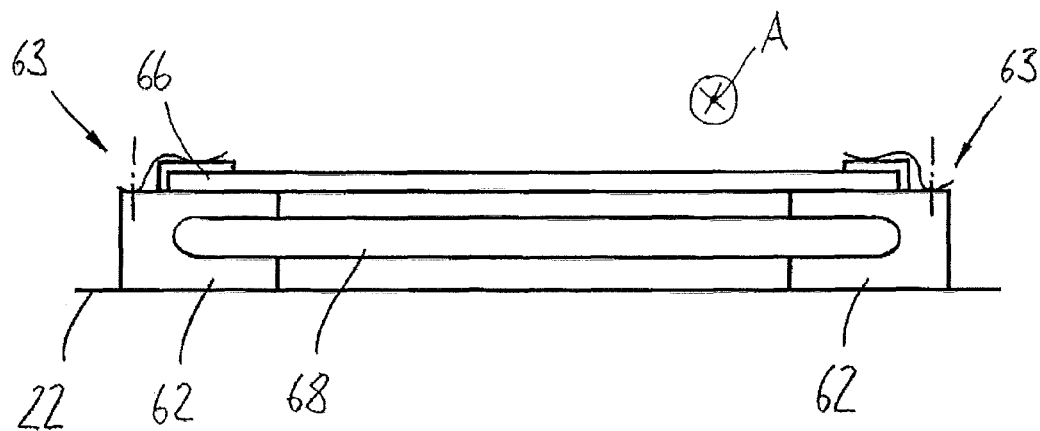
Figure 6:
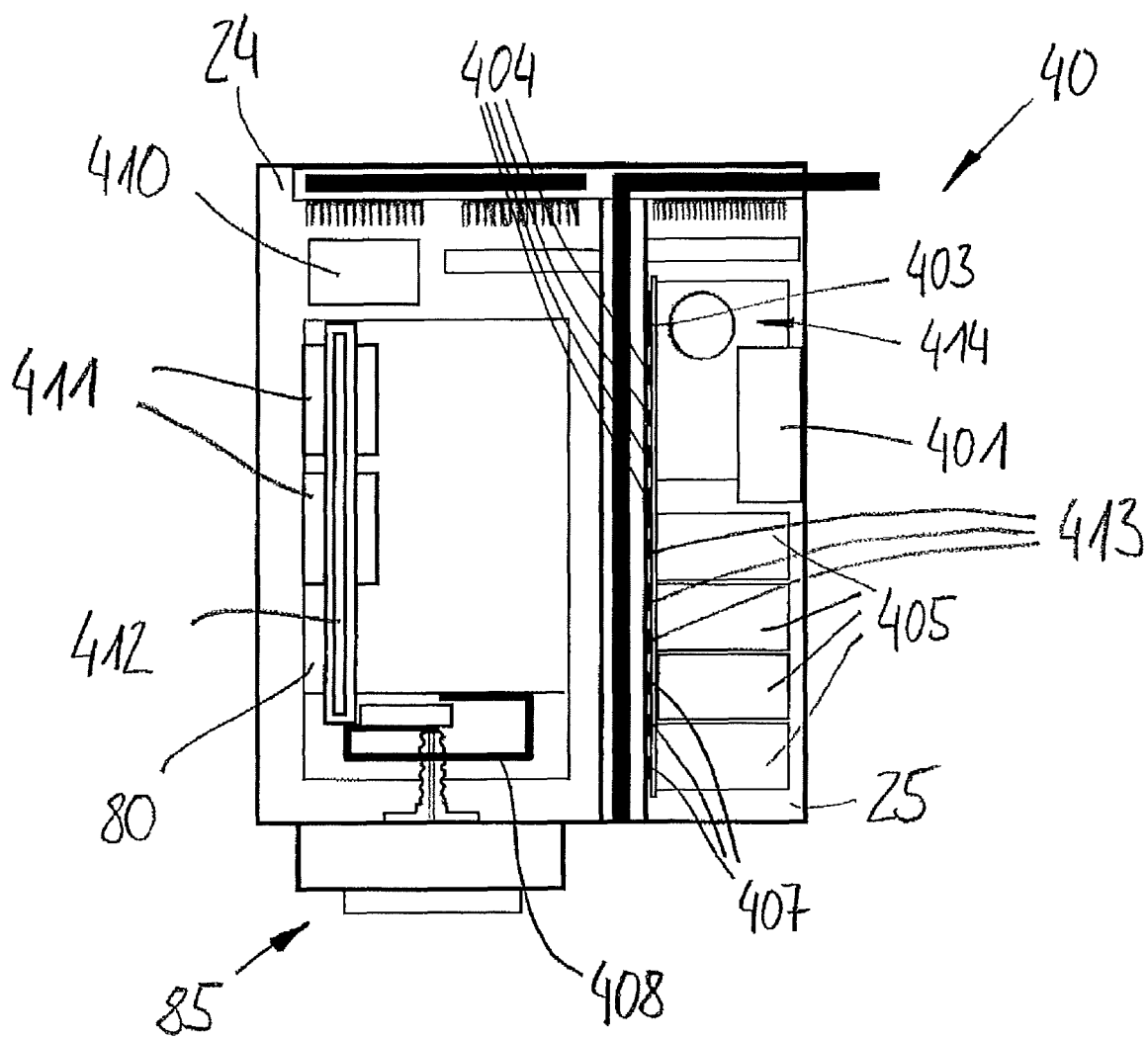
Figure 7:
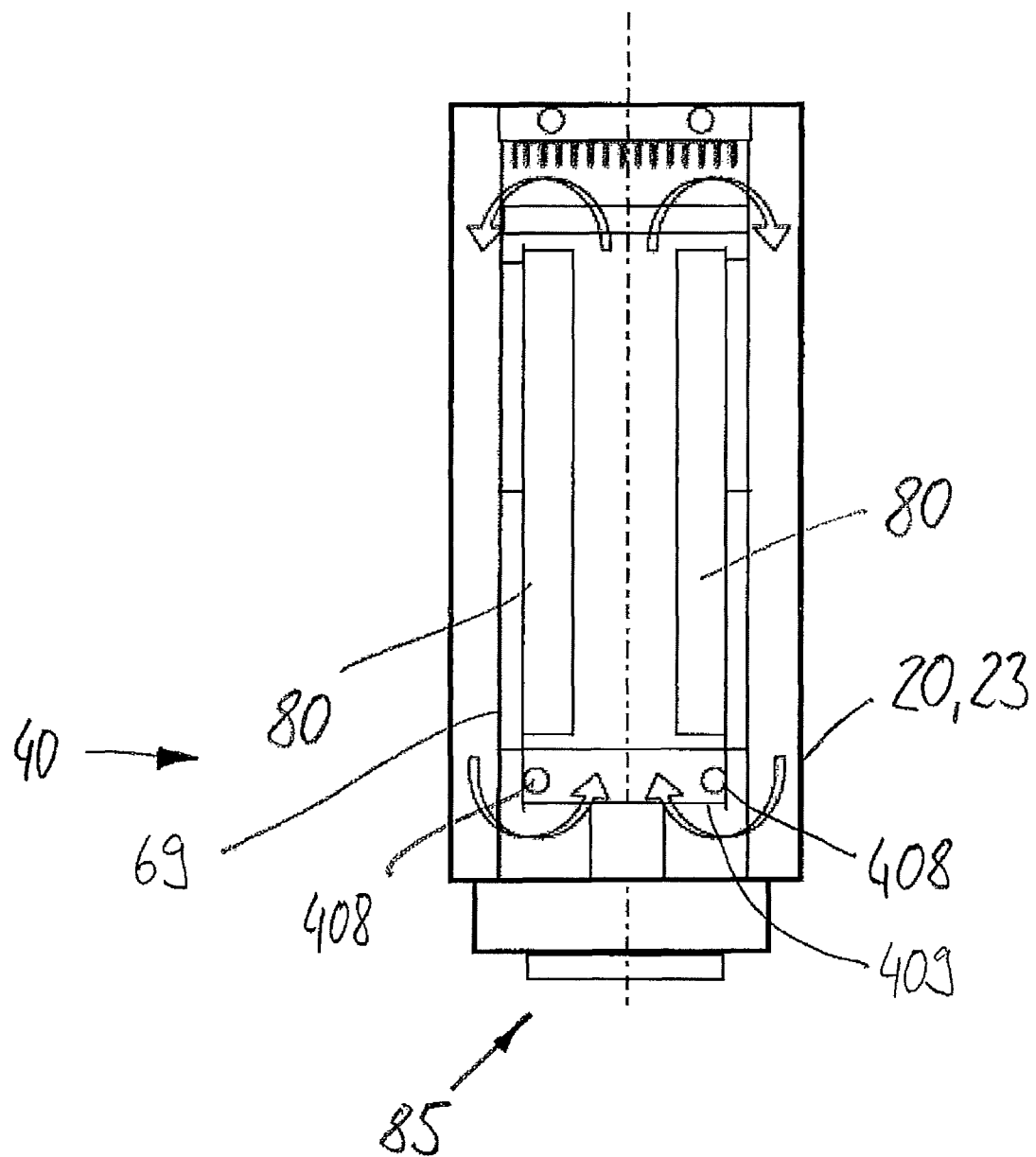
Figure 8:
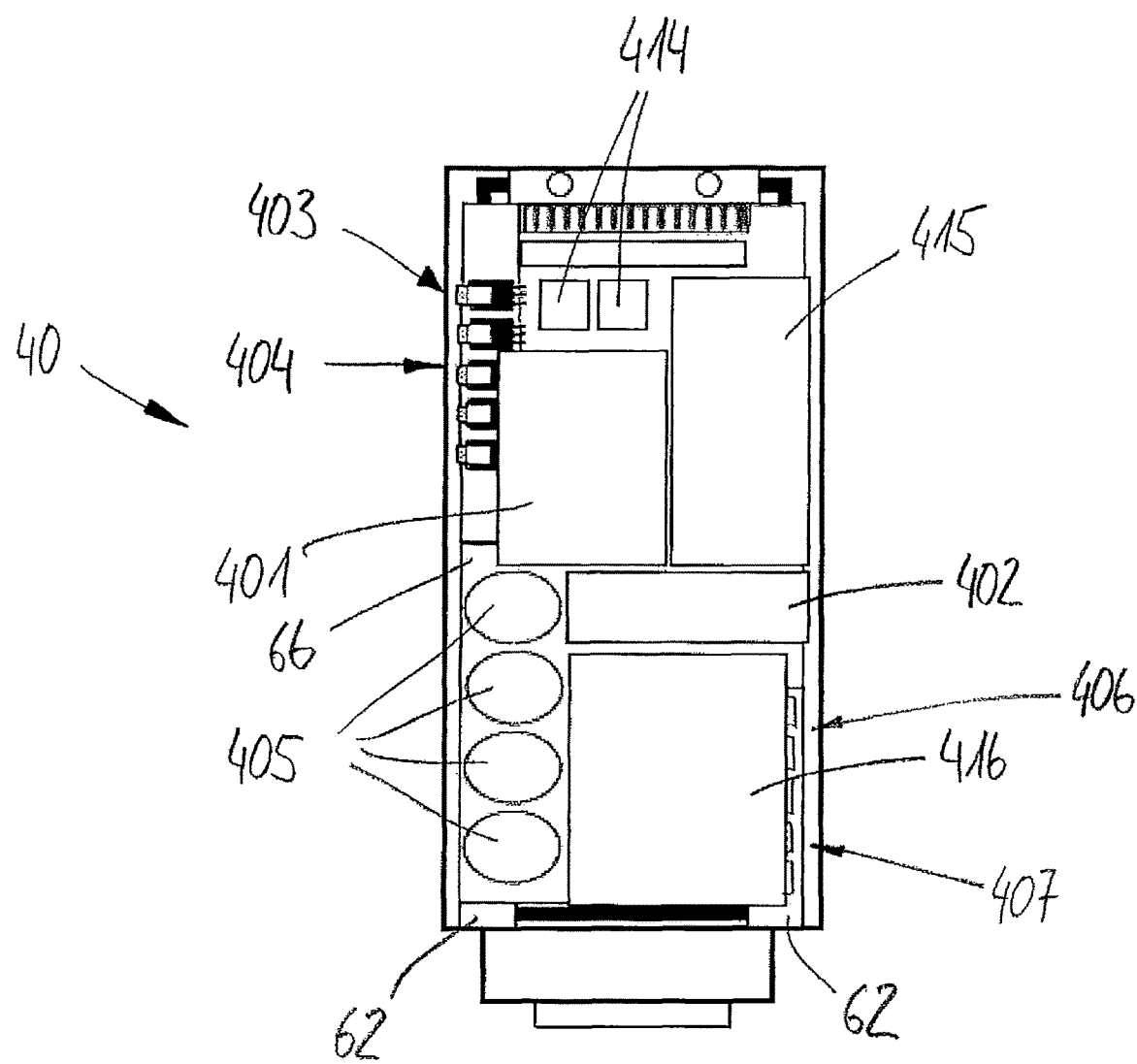
Figure 9:
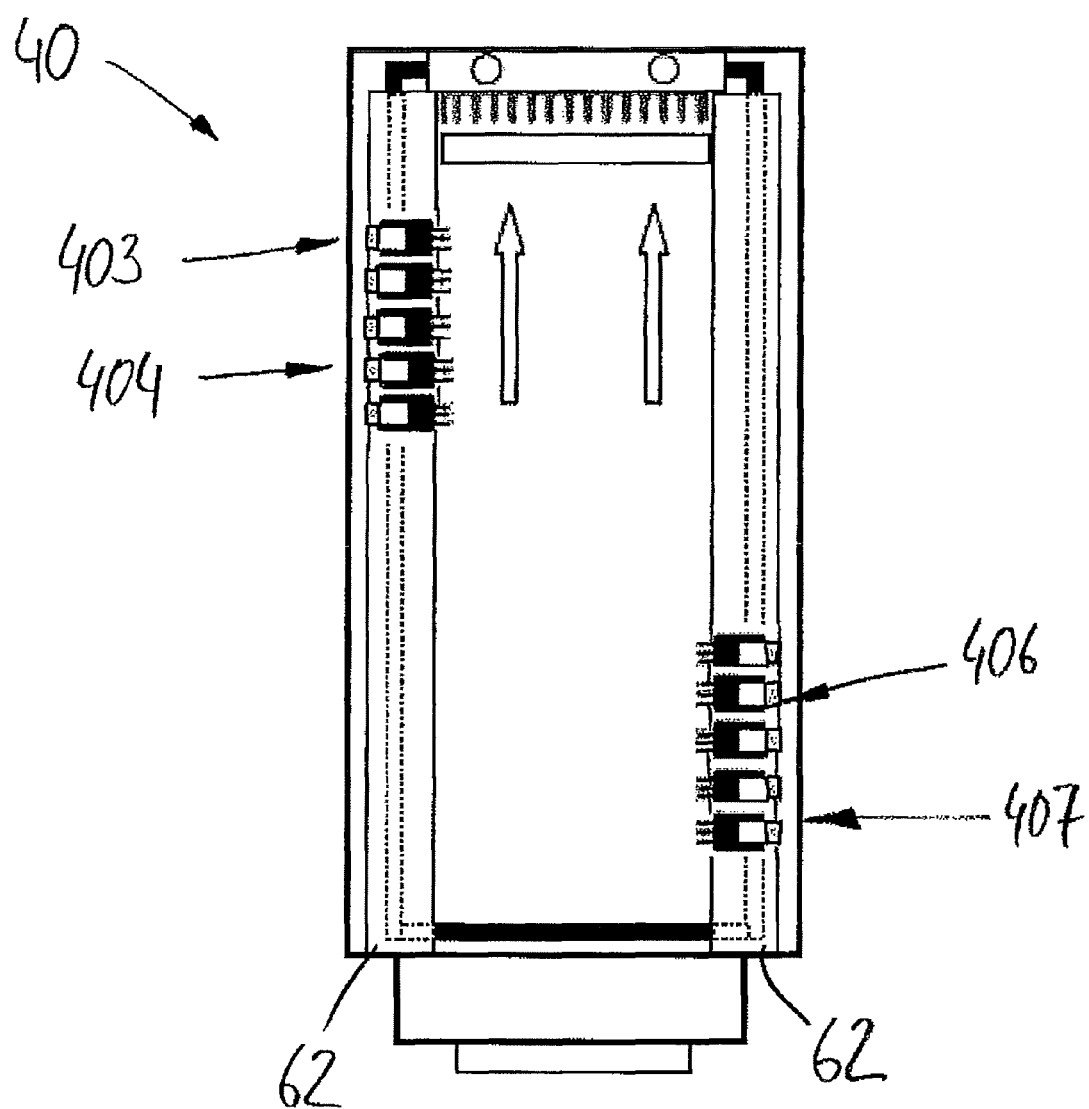
Figure 10A:
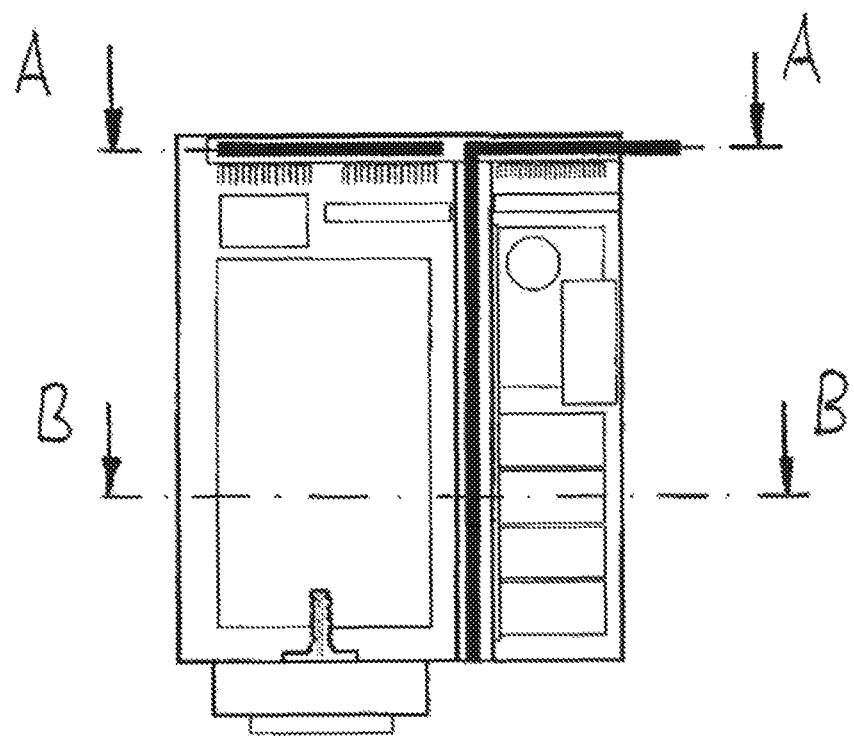
Figure 10B:
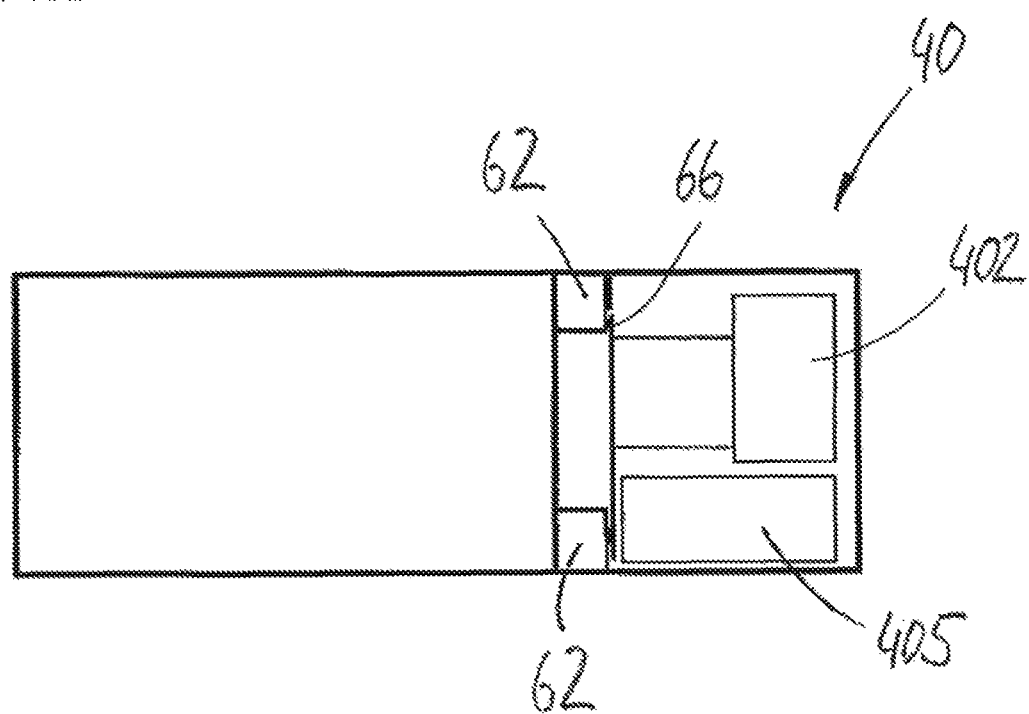
Figure 10C:
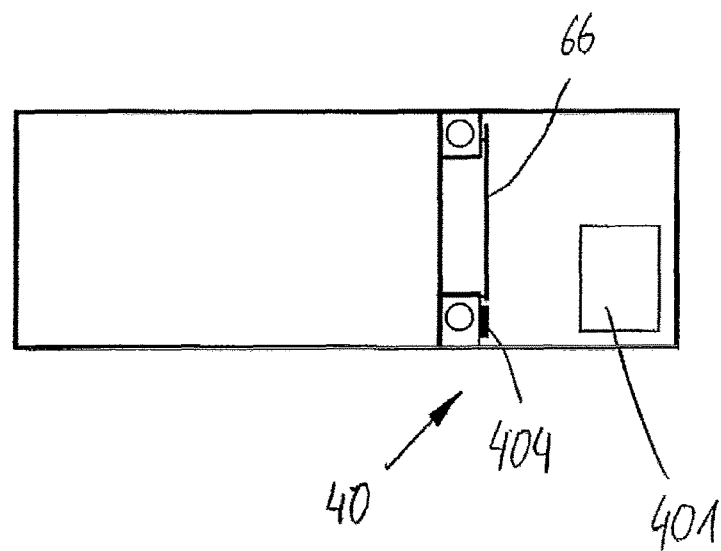
Figure 11:
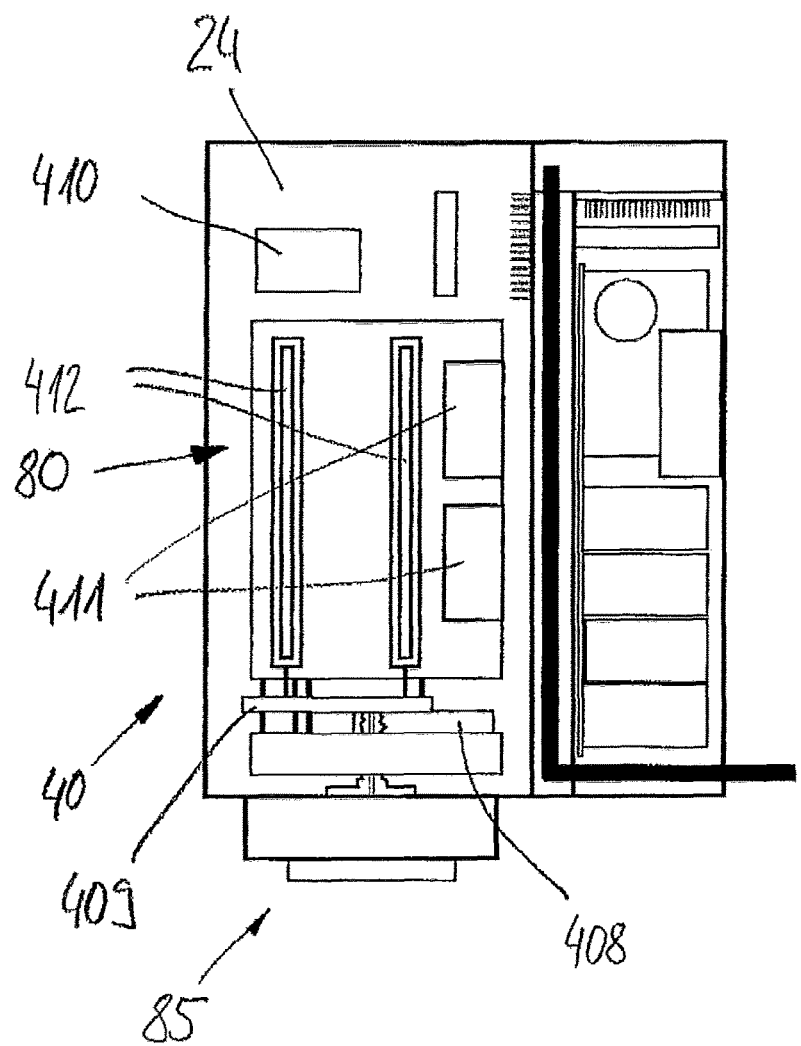

FIG. 1a: shows a schematic sectioning of a first preferred embodiment of a power supply unit in a side view;

FIG. 1b: shows a top view of the preferred embodiment of FIG. 1a;

FIG. 1c: shows a sectioning A-A as indicated in FIG. 1b;

FIG. 2a: shows the preferred embodiment according to FIG. 1a in a side view indicating two sectionings A-A and B-B;

FIG. 2b: shows the sectioning A-A as indicated in FIG. 2a;

FIG. 2c: shows the sectioning B-B as indicated in FIG. 2a;

FIG. 3a: shows a side view of the preferred embodiment according to FIG. 1a indicating two sectionings A-A and B-B;

FIG. 3b: shows the sectioning A-A as indicated in FIG. 3a;

FIG. 3c: shows the sectioning B-B as indicated in FIG. 3a;

FIG. 4: shows a schematic sectioning of a further preferred embodiment of a power supply unit in a side view;

FIG. 5: shows a top view along a longitudinal axis of a board that is arranged at two plates;

FIG. 6: shows an arrangement of an electric system in a first and a second chamber according to one or more embodiments;

FIG. 7: shows an arrangement of parts of the electric system according to the embodiment shown in FIG. 6 (cf. also to FIG. 1c);

FIG. 8: shows a preferred arrangement of parts of an electric system in the second chamber according to the embodiment shown in FIG. 6 (cf. also to FIG. 2b, sectioning A-A);

FIG. 9: shows a preferred arrangement of parts of the electric system in the second chamber according to the preferred embodiment shown in FIG. 6 (cf. also to FIG. 2c, sectioning B-B);

FIG. 10a: shows the embodiment of FIG. 1a in a side view indicating two sectionings A-A and B-B;

FIG. 10b: shows the sectioning A-A according to FIG. 10a;

FIG. 10c: shows the sectioning B-B according to FIG. 10a;

FIG. 11: shows a preferred arrangement of parts of the electric system of the preferred embodiment of the power supply unit according to FIG. 4.

FIG. 1a shows a schematic sectioning of a first embodiment of a power supply unit in a side view. The power supply unit comprises a housing 20 with outer walls 23 and an inner wall 22. The inner wall 22 separates the housing 20 in a first chamber 24 and a second chamber 25. Both chambers 24, 25 are filled with an insulation gas 50, in particular nitrogen. The nitrogen is pressurized. The pressure lies expediently within a range of about 2 to 3 bar, meaning 1 to 2 bar above the normal pressure of 1013 mbar. The housing 20 as well as the chambers 24 and 25 extend along an axis A. At a bottom end of the housing 20, the power supply unit comprises a high voltage output connector 85. Within the first chamber 24 there is located a voltage multiplier 80 that comprises a lower voltage area 82 (e.g. up to 70-90 kV) and a higher voltage area 84 (e.g. 80-150 kV). Lower voltage area 82 comprises elements, either discrete or integrated, which operate at a lower voltage compared to the elements arranged in the higher voltage area 84 of multiplier 80.

The lower voltage area 82 is oriented towards a top end of the housing 20, wherein the higher voltage area 84 of the voltage multiplier 80 is oriented or directed respectively towards a bottom end of the housing 20 or the first chamber 24, respectively. The first chamber 24 as well as the second chamber 25 comprise means 26 for conveying the insulation gas 50.

Above the means 26 for conveying the insulation gas 50 or the fans 26, respectively, a plate 62 is arranged. The plate 62 is a part of a heat absorber unit 60 that also comprises at least three heat exchange elements 64 that are arranged at the horizontal plate 62. Performance values (nitrogen to water) of the heat exchange elements 64 in the first chamber 24 lie within a range of about 200 W, wherein a performance (nitrogen to water) of the heat exchange element 64 in the second chamber 25 preferably lies within a range of about 60 W. Advantageously, the heat absorber unit 60 provides a temperature drop of the insulation gas 50 of about 20° C. A further vertical plate 62 is arranged at the inner wall 22. The plate 62 comprises cooling channels 68 that are, for example, filled with water to absorb and transfer the heat, in particular of an electric system 40. The cooling channels 68 comprises appropriate cooling channel inputs and/or outputs 68' that are adapted to be connected to e.g. a cooling medium supply system. The different parts of the electric system 40 are for example described in the FIGS. 6, 7, 8 and 9.

FIG. 1b shows a top view along the axis A of the embodiment of a power supply unit according to FIG. 1a. A dotted line indicates the inner wall 22 that separates the housing 20 in the first chamber 24 and in the second chamber 25. A section A-A is explained in FIG. 1c.

FIG. 1c shows the sectioning A-A as indicated in FIG. 1b. The first chamber 24 comprises the plate 62 that is arranged at the outer wall 23 of the housing 20. The plate 62 comprises two cooling channels 68. The heat exchange element 64 is arranged or attached, respectively, to the plate 62. Below the heat exchange element 64 there is located the fan 26. The fan 26 generates an insulation gas flow 52, in particular a circulating insulation gas flow 52 as FIG. 1c shows. Two voltage multipliers 80 extend along the longitudinal axis A. They are arranged at a supporting structure 69. The circulating gas flow 52 moves from the top of the housing 20 to the bottom of the housing 20 along the outer wall 23, wherein the circulating insulation gas flow 52 moves from the bottom end of the housing 20 to the top end of the housing 20 passing the voltage multipliers 80. Advantageously, the whole first chamber 24 is filled with the insulation gas 50.

FIG. 2a shows the embodiment of FIG. 1a indicating two sectionings A-A and B-B that are explained in the next Figures.

FIG. 2b shows the sectioning A-A as indicated in FIG. 2a. The second chamber 25 is filled with the insulation gas 50. The two vertical plates 62 extend along the axis A. The further horizontal plate 62 that is arranged at the top end of the housing 20 is connected with the above mentioned plates 62 via the cooling channels 68. The two vertical plates 62 are also connected by a cooling channel 68 at the bottom end of the housing 20. The heat exchange element 64 is arranged at on of the vertical plates 62. Above the heat exchange element 64, the fan 26 is located. The different parts of the electric system 40 are for example described in FIG. 8.

FIG. 2c shows a sectioning B-B as indicated in FIG. 2a. Especially, the parts of the electric system 40 as shown in FIG. 2b are no longer there so that the two vertical plates 62 are visible. In particular, the arrangement of the cooling channels 68 can be seen. The fan 26 generates an insulation gas flow 55 as for example indicated by the arrows in FIG. 2c.

FIG. 3a shows the embodiment of the power supply unit according to FIG. 1a indicating two sectionings A-A and B-B.

FIG. 3b shows the sectioning A-A as indicated in FIG. 3a. The first chamber 24 and the second chamber 25 are shown in a top view. Thus, the fans 26 are shown in a top view. The first chamber 24 and the second chamber 25 are separated by the inner wall 22. At the inner wall 22 there are arranged the plates 62 that are a part of the heat absorber unit 60. The heat absorber unit 60 comprises cooling channels 68. The small arrows indicate a possible flow direction of a cooling medium, such as water, that flows inside the cooling channels 68.

FIG. 3c shows the sectioning B-B as indicated in FIG. 3a. The Figure shows that a board 66 is arranged at the plates 62. The board 66 is for example a power converter board. The board 66 can be in direct contact with the plates 62. However, the board 66 does not have to be directly attached to the plates 62. The plates 62 are provided with the cooling channels 68.

FIG. 4 shows a schematic sectioning of another embodiment of a power supply unit with a housing 20. This embodiment is widely similar to that one shown in FIG. 1a. However, a structure of a voltage multiplier 80 is different. Nevertheless, the voltage multiplier 80 comprises in the same way a lower voltage area 82 and a higher voltage area 84 that represents a heat source 70 (similar to the embodiment shown in FIG. 1a). A heat absorber unit 60 comprises the elements as already known from FIG. 1a, however plates 62 and cooling channels 68 are arranged differently. As a consequence, a cooling channel input/output 68' is arranged at a bottom end of the housing 20. A further difference to the embodiment showing in FIG. 1a is an arrangement of a fan 26 in the first chamber 24. As a consequence, a heat exchange element 64 in the first chamber 24 is mounted or arranged, respectively, at an inner wall 22. The arrangement of an electric system 40 in a second chamber 25 corresponds to the one shown in FIG. 1a.

FIG. 5 shows an arrangement of a board 66, in particular a power converter board, at two plates 62. The two plates 62 are connected by a cooling channel 68. Furthermore, the two plates 62 are arranged at an inner wall 22. A form and/or force fit connection between the board 66 and the plates 62 is realized by appropriate connection elements 63 that are e.g. formed as clips.

FIG. 6 explains the electric system 40 of the embodiment as shown in FIG. 1a in more detail. The first chamber 24 comprises a high voltage transformer 410. Between the voltage multiplier 80 and the high voltage output connector 85 there is arranged a spark current limiter 408. Furthermore, the first chamber 24 comprises a high voltage measurement divider 412 and a filament transformer and rectifier 411. The second chamber 25 comprises a plurality of input electrolytic capacitors 405. In addition, a plurality of PFC (Power Factor Correction) and soft start semiconductor components 404 as well as a plurality of high voltage converter components 413 are arranged in the second chamber 25. In addition, a power supply 401 for the filament converter, a PFC conductor 414 and rectifiers 403 are provided.

FIG. 7 shows the sectioning as already known from FIG. 1c. Two voltage multipliers 80 are arranged at a structure 69 that is in contact with the housing 20 or the outer wall 23 respectively. The two voltage multipliers 80 are connected via an interconnection board 409. In this view, also two spark current limiters 408 are visible.

FIG. 8 shows the sectioning as already known from FIG. 2b. PFC inductors 414, a line filter 415, a power supply 402 for a control board 416 as well as the input electrolytic capacitors 405 are arranged at a board 66. Rectifiers 403, PFC and soft start semiconductor components 404 as well as the filament converter components 407 are directly mounted at the plate 62.

FIG. 9 shows the sectioning as already known from FIG. 2c. It can be seen that the rectifiers 403, the PFC and soft start semiconductor components 404, the converter semiconductor components 406 as well as the filament converter components 407 are directly arranged at the plates 62. These components are the power electronic components. The remaining components shown in FIG. 8 are the control system components. The gas flow introduced by the fan transports the heat towards from the converter components towards the upper portion. At the same time the gas prevents electrical discharge on the components and reduces corona around the components allowing for a compact arrangement of the converter components.

FIG. 10a shows the already known sectioning of the embodiment of FIG. 1a indicating two sectionings as already known from FIG. 3a.

FIG. 10b shows the power supply 402 for the control board 416 in a top view as well as an input electrolytic capacitor 405.

FIG. 10c shows the power supply 401 for the filament converter in a top view.

FIG. 11 shows the further embodiment of a power supply unit that is already known from FIG. 4, explaining an electric system 40 of the first chamber 24 more detailed. In particular, the arrangement of filament transformers and rectifiers 411 and high voltage measurement dividers 412 is different to the one shown in FIG. 6. The different design of the voltage multiplier 80 leads also to a different arrangement or design of an interconnection board 409. Also a spark current limiter 408 is designed differently to the one as for example shown in FIG. 6.

REFERENCE NUMERALS 10 electron beam emitter
20 housing
22 inner wall
23 outer wall
24 first chamber
25 second chamber
26 means for conveying gas, fan
40 electric system
401 power supply for filament converter
402 power supply for control board
403 rectifier
404 PFC (Power Factor Correction) and soft start semiconductor components
405 input electrolytic capacitors
406 converter semiconductor components
407 filament converter components
408 spark current limiter
409 interconnection board
410 HV (High Voltage) transformer
411 filament transformer and rectifier
412 HV (High Voltage) measurement divider
413 HV (High Voltage) converter components
414 PFC inductors
415 line filter
416 control board
50 gas, nitrogen
52 insulation gas flow
60 heat absorber unit
62 plate
63 connection element
64 heat exchange element
66 (power converter board) board
68 cooling channel
68' cooling channel input/output
69 supporting structure 70 heat source
80 voltage multiplier
82 lower voltage area
84 higher voltage area
85 high voltage output connector
A (longitudinal) axis

The invention claimed is:

1. Power supply unit for a sterilization device, comprising:
- a housing;
- an electric system, the electric system being arranged within the housing and being configured to provide a high output voltage to a high voltage output connector attached to the housing, and the housing is filled with an insulation gas that electrically insulates the electric system; and
- a heat absorber unit, the heat absorber unit comprising at least one heat exchange element arranged at at least one plate,
- wherein parts of the electric system are arranged on a board, and wherein the board is arranged at the heat absorber unit.

2. Power supply unit according to claim 1, wherein the housing is substantially sealed to allow the insulation gas to be pressurized.

3. Power supply unit according to claim 1, wherein the housing comprises an inner wall, separating the housing into a first chamber and a second chamber, and
wherein the at least one plate of the heat absorber unit is arranged at the inner wall.

4. Power supply unit according to claim 1, wherein the heat absorber unit comprises at least one cooling channel, and wherein the cooling channel is configured to cool the at least one heat exchange element, the board and/or the at least one plate.

5. Power supply unit according to claim 1, wherein the housing comprises means for conveying the insulation gas throughout the housing wherein the conveyed insulation gas provides a cooling effect onto the electric system.

6. Power supply unit according to claim 5, wherein the housing comprises at least one heat source being part of the electric system, wherein the means for conveying the insulation gas are adapted to establish an insulation gas flow that is directed at least from the at least one heat source to the at least one heat exchange element.

7. Power supply unit according to claim 5, wherein the insulation gas flow is a circulating insulation gas flow.

8. Power supply unit according to claim 1, wherein the electric system comprises a voltage multiplier.

9. Power supply unit according to claim 8, wherein the voltage multiplier comprises at least a first area and a second area, wherein on the first area elements are arranged operating at a lower voltage than elements arranged on the second area, wherein the first area is orientated or directed, respectively, towards the at least one heat exchange element.

10. Sterilization device, in particular for packaging material, comprising an electron beam emitter and a power supply according to claim 1, wherein the electric system is connected via the high voltage output connector to the electron beam emitter.

11. Power supply unit according to claim 1, wherein the insulation gas is nitrogen.

12. Power supply unit according to claim 1, wherein the board is arranged at the at least one plate.

13. Power supply unit according to claim 1, wherein the housing comprises a fan for conveying the insulation gas throughout the housing so that the insulation gas provides a cooling effect onto the electric system.

14. Method to electrically insulate a power supply unit in a sterilization device with an insulation gas comprising a housing and an electric system, said electric system being configured to provide a high output voltage to a high voltage output connector attached to the housing, wherein the insulation gas is configured to electrically insulate the electric system, wherein the electric system is located within the housing, wherein the power supply unit includes a heat absorber unit, the heat absorber unit comprising at least one heat exchange element arranged at at least one plate, wherein parts of the electric system are arranged on a board, and wherein the board is arranged at the heat absorber unit, the method comprising:
- reducing air pressure inside the housing; and
- filling the housing with the insulation gas.

15. Method according to claim 14, wherein the filling of the housing with the insulation gas includes filling the housing with nitrogen gas.

* * * * *